US009340752B2

(12) United States Patent
Brask et al.

(10) Patent No.: US 9,340,752 B2
(45) Date of Patent: May 17, 2016

(54) ENZYMATIC REMOVAL OF STERYL GLYCOSIDES IN FATTY ACID ALKYL ESTERS

(75) Inventors: Jesper Brask, Bagsvaerd (DK); Per Munk Nielsen, Hilleroed (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 13/254,012

(22) PCT Filed: Mar. 5, 2010

(86) PCT No.: PCT/EP2010/052807
§ 371 (c)(1),
(2), (4) Date: Sep. 21, 2011

(87) PCT Pub. No.: WO2010/102952
PCT Pub. Date: Sep. 16, 2010

(65) Prior Publication Data
US 2012/0009659 A1    Jan. 12, 2012

Related U.S. Application Data

(60) Provisional application No. 61/158,472, filed on Mar. 9, 2009.

(30) Foreign Application Priority Data

Mar. 9, 2009   (EP) .................................... 09154639

(51) Int. Cl.
| | |
|---|---|
| *C11C 1/08* | (2006.01) |
| *C12S 3/18* | (2006.01) |
| *C07J 17/00* | (2006.01) |
| *C10L 1/02* | (2006.01) |
| *C10L 1/10* | (2006.01) |
| *C10L 1/238* | (2006.01) |
| *C10L 10/00* | (2006.01) |
| *C11C 3/00* | (2006.01) |
| *C10L 1/12* | (2006.01) |
| *C10L 1/16* | (2006.01) |
| *C10L 1/196* | (2006.01) |

(52) U.S. Cl.
CPC .............. *C11C 1/08* (2013.01); *C07J 17/005* (2013.01); *C10L 1/026* (2013.01); *C10L 1/10* (2013.01); *C10L 1/2381* (2013.01); *C10L 10/00* (2013.01); *C11C 3/003* (2013.01); *C10L 1/12* (2013.01); *C10L 1/165* (2013.01); *C10L 1/1641* (2013.01); *C10L 1/1963* (2013.01); *C10L 2200/0476* (2013.01); *Y02E 50/13* (2013.01)

(58) Field of Classification Search
None
See application file for complete search history.

(56) References Cited

U.S. PATENT DOCUMENTS

| | | |
|---|---|---|
| 2007/0175091 A1 | 8/2007 | Danzer et al. |
| 2011/0099889 A1 | 5/2011 | Sohling et al. |

FOREIGN PATENT DOCUMENTS

| | | |
|---|---|---|
| EP | 2098585 A1 | 9/2009 |
| JP | 8070885 | 3/1996 |
| WO | WO 2007/076163 A2 | 7/2007 |
| WO | WO 2008/051984 A2 | 5/2008 |
| WO | WO 2010/004423 A2 | 1/2010 |

OTHER PUBLICATIONS

Brenda, comprehensive enzyme Information System, EC 3.1.1.3-triacylglycerol lipase, accessed Sep. 18, 2012 at www.brenda-enzymes.org/php/result_flat.php4?ecno=3.1.1.3.*
Sheldon (2007) Enzyme Immobilization: The Quest for Optimum Performance, Adv. Synth. Catal., 349, 1289-1307.*
Hanefeld et al., Understanding enzyme immobilization, Chemical Society Reviews, 38, 453-468.*
Lee et al. (2004) Emission reduction potential from the combustion of soy methyl ester fuel blended with petroleum distillate fuel, Fuel, 83, 1607-1613.*
Merriam Webster, definition of zoosterol, Accessed Jan. 22, 2013, online at: www.merriam-webster.com/medical/zoosterol.*
Sorenson et al., Determination of Campesterol, Stigmasterol, and beta-Sitosterol in Saw Palmetto Raw Materials and Dietary Supplements by Gas Chromatography: Single-Laboratory Validation, J AOAC Int., 2006; 89(1): 22-34.*
Lee et al., The Role of Sterol Glucosides on Filter Plugging, Biodiesel Magazine, Apr. 6, 2007, available online at: www.biodieselmagazine.com/articles/1566/the-role-of-sterol-glucosides-on-filter-plugging/.*
Ferrari et al, JAOCS, vol. 74, No. 2, pp. 93-96 (1997).
Forsee et al, Arch Biochem Biophys, vol. 172, No. 2, pp. 410-418 (1976).
Lee et al, Internet Citation retrieved from biodieselmagazine.com/article.jsp?article_id=1566&q=sterol%20glucosides&category_id=14, pp. 1-3 (2008).
Moreau et al, JAOCS, vol. 85, No. 8, pp. 761-770 (2008).
Nystrom et al, Eur Food Res Technol, vol. 227, pp. 727-733 (2008).
Paczkowski et al, Biotechnol Lett, vol. 29, pp. 1403-1408 (2007).
Tang et al, Fuel, vol. 87, pp. 3006-3017 (2008).
Van Hoed et al, JAOCS, vol. 85, No. 8, pp. 701-709 (2008).
JP 08-070885, Database WPI—Access No. 1996-203163, 2 pages (1996).
Murui Tateo et al, Enzymatic Acylation of Sterylglycosides, vol. 44, No. 3 pp. 211-214 (1995).
Murui et al, Enzymatic Acylation of Sterylglycosides, vol. 44, No. 3 pp. 211-213 (1995).

* cited by examiner

*Primary Examiner* — Karen Cochrane Carlson
*Assistant Examiner* — Jennifer M. H. Tichy
(74) *Attorney, Agent, or Firm* — Kristin McNamara

(57) ABSTRACT

The present invention relates to a process of reducing the content of steryl glycoside in a bio-diesel composition which comprises a step of contacting the composition with an enzyme being capable of acylating the steryl glycoside.

20 Claims, No Drawings

ENZYMATIC REMOVAL OF STERYL GLYCOSIDES IN FATTY ACID ALKYL ESTERS

CROSS-REFERENCE TO RELATED APPLICATIONS

This application is a 35 U.S.C. 371 national application of PCT/EP2010/052807 filed Mar. 5, 2010, which claims priority or the benefit under 35 U.S.C. 119 of European application no. 09154639.0 filed Mar. 9, 2009 and U.S. provisional application No. 61/158,472 filed Mar. 9, 2009, the contents of which are fully incorporated herein by reference.

FIELD OF THE INVENTION

The invention relates to the field of biodiesel and methods of reducing the content of steryl glycoside in biodiesel.

BACKGROUND OF THE INVENTION

Insoluble contaminants may appear as haze, precipitates or sediments in biodiesel produced from various feedstock of vegetable and animal origin. This may prevent the product from complying with the requirements on contamination and filterability according to the biodiesel quality standards e.g. in Europe (EN 14214), US (ASTM D6751) and Germany (DIN 51606). The appearance of haze, precipitates or sediments have been found amongst other parameters to be linked to the presence of free steryl glycosides as described in Van Hoed, V. et al. "Identification and occurrence of steryl glucosides in palm and soy biodiesel." J Am Oil Chem Soc (2008) vol. 85: p. 701-709; Moreau, R A. et al. "The identification and quantification of steryl glucosides in precipitates from commercial biodiesel." J Am Oil Chem Soc (2008) vol. 85: p. 761-770; and Tang, H. et al. "Fuel properties and precipitate formation at low temperature in soy-, cottonseed-, and poultry fat-based biodiesel blends." Fuel 87 (2008) 3006-3017.

Accordingly, removal of steryl glycosides from biodiesel is therefore often necessary and a few methods based on filtering or adsorption have been described in WO 2007/076163 which describes a process for treating biodiesel comprising placing biodiesel in contact with a compound capable of removing steryl glycosides from the biodiesel by adsorption; US 2007/0175091 which describes a method for removing impurities from biodiesel comprising: (a) converting a feedstock into biodiesel having a temperature exceeding 98° C.; (b) cooling the biodiesel to a temperature range sufficient to form particulates of impurities; and (c) filtering the cooled biodiesel to remove the particulates; and WO 2008/051984 which describes a method of passing a biodiesel stream through a filter having a molecular weight cut-off of less than 1,000,000 g/mol.

However, these methods of physically removing steryl glycosides are associated with a yield loss of biodiesel. Hence, there is still a need for alternative processes to remove steryl glycosides from biodiesel with low yield-loss, to provide products that are able to meet the biodiesel quality standards on contamination and filterability and which do not suffer from fuel filter plugging problems.

JP08070885A (Nisshin Oil Mills Ltd.) (Database WPI/Thomson AN 1996-203163) discloses a method of manufacturing an acylated steryl glycoside for use in health foods, drugs, agrochemicals and cosmetics which comprises reacting the steryl glycoside with a fatty acid in an aqueous solution containing a lower alcohol or chloroform in the presence of a lipase.

SUMMARY OF THE INVENTION

The object of the present invention is to provide a process of reducing the content of steryl glycosides from fatty acid alkyl ester compositions.

The inventors have surprisingly found that enzymatic catalysis using an enzyme being capable of acylating the steryl glycoside can be used to reduce the content of contaminating steryl glycoside from a composition primarily consisting of fatty acid alkyl ester. The enzymatic catalysis is useful for removing even small amounts of steryl glycoside from such compositions. The fatty acid alkyl ester in the composition can be used as acyl donor to acylate steryl glycoside to soluble acylated steryl glycoside.

In one aspect the invention therefore relates to a process of reducing the content of steryl glycoside in a composition comprising fatty acid alkyl ester, wherein at least 80 wt. % of fatty acids in the composition are in the form of fatty acid alkyl ester, which comprises a step of contacting the composition with an enzyme being capable of acylating the steryl glycoside In another aspect the invention relates to use of such process for reducing the filter blocking tendency in fuel and/or fuel blends.

DETAILED DESCRIPTION OF THE INVENTION

The inventors have surprisingly discovered that steryl glycoside present in fatty acid alkyl ester compositions may be removed enzymatically. This is obtained by converting the steryl glycoside into its acylated form by enzymatic catalysis in the presence of an acyl donor which may be the fatty acid alkyl ester which is the main constituent of the fatty acid alkyl ester composition. The examples demonstrate that in biodiesel the content of steryl glycoside may be reduced in the presence of an enzyme with a simultaneously increase in the content of acylated steryl glycoside.

In some embodiments the invention relates to a process of removing steryl glycoside from a fatty acid alkyl ester composition comprising: reacting the steryl glycoside with a lipase in the presence of an acyl donor. Preferably, at least 80 wt. % of fatty acids in such composition are in the form of fatty acid alkyl ester.

In some embodiments the invention relates to a process of reducing the content of steryl glycoside in a composition comprising fatty acid alkyl ester, wherein at least 80 wt. % of fatty acids in the composition are in the form of fatty acid alkyl ester, which comprises a step of contacting the composition with an enzyme being capable of acylating the steryl glycoside.

Preferably, at least 85 wt. % of fatty acids in the composition are in the form of fatty acid alkyl ester, more preferably at least 90 wt. %, and even more preferably at least 95 wt. %.

Preferably, the composition comprises at least 85 wt. % fatty acid alkyl ester, more preferably 90 wt. %, and even more preferably at least 95 wt. %. However, the composition may also be a blend of fatty acid alkyl ester, such as biodiesel, and petroleum-based diesel. I.e., the bio-diesel may be blended with petroleum-based diesel before, during or after the enzymatic reaction.

Sterols, Steryl Glycosides (SG) and Acylated Steryl Glycosides (ASG)

Sterols are an important class of organic molecules which occur naturally in both plants and animals. Sterols of plants are called phytosterols such as campesterol, sitosterol, stigmasterol, avenasterol, brassicasterol, desmosterol, fucosterol, and sargasterol, and sterols of animals are called zoosterols such as cholesterol and some steroid hormones. Ergosterol is a sterol present in the cell membrane of fungi, where it serves a role similar to cholesterol in animal cells.

Sterols are also known as steroid alcohols. They are a subgroup of steroids with a hydroxyl group at the 3-position of the A-ring. They are amphipathic lipids synthesized from acetyl-coenzyme A via the HMG-CoA reductase pathway. The overall molecule is quite flat. The hydroxyl group on the A ring is polar. The rest of the molecule is non-polar.

It is understood that the corresponding saturated form of sterols, denominated stanols, are also included in the present invention. Without being limiting, examples of phytostanols are such as campestanol, sitostanol, stigmastanol, avenastanol, desmostanol, sargastanol, brassicastanol and fucostanol, and examples of zoostanols are such as cholestanol, etc.

Steryl glycosides, also sometimes referred to as steryl glucosides, sterol glycosides, sterol glucosides, sterolins, or free steryl glycosides (FSG), comprise a sterol group linked to a carbohydrate at the hydroxyl moiety of the sterol. The steryl glycosides containing a fatty acid esterified to the primary hydroxyl group of the carbohydrate moiety are described as acylated steryl glycosides.

Both steryl glycosides and acylated steryl glycosides are naturally occurring compounds in plants where acylated steryl glycosides are more abundant than (non-acylated) steryl glycosides. An example of an acylated steryl glycoside present in soybean is 6'-linoleoyl-beta-D-glucoside of beta-sitosterol. Examples of fatty acids present in acylated steryl glycosides are the fatty acids present in plants or animals such as palmitic acid, oleic acid, stearic acid, linoleic acid and linolenic acid.

Steryl glycosides are mainly present as monoglycosides although diglycosides may also be present. A common sugar in steryl glycosides is D-glucose, but other monosaccharides such as arabinose, fructose, galactose, mannose, and xylose may also be found in steryl glycosides.

In some embodiments the invention relates to a process, wherein the steryl glycoside is derived from a sterol selected from a group consisting of: Phytosterol such as campesterol, sitosterol, stigmasterol, avenasterol, brassicasterol, desmosterol, fucosterol, and sargasterol; zoosterols such as cholesterol; the corresponding saturated forms of said sterols (stanols); and any combinations thereof.

In some embodiments the invention relates to a process, wherein the steryl glycosides comprises a monosaccharide selected from the group containing, preferably from the group consisting of: arabinose, fructose, galactose, glucose, mannose, and xylose.

Precipitation in Biodiesel

Biodiesel represents a promising alternative fuel for use in compression-ignition (diesel) engines. The biodiesel standards (DIN 51606, EN 14214, and ASTM D6751) require or indirectly specify that biodiesel should be fatty acid esters or even fatty acid methyl esters (FAME). However, we will use the term biodiesel broadly for fatty acid alkyl esters of short-chain alcohols, where a short-chain alcohol is an alcohol having 1 to 5 carbon atoms ($C_1$-$C_5$).

Development of an amorphous cloud-like substance and precipitate formation in biodiesel are known and may cause flow problems or fuel filter blockages in the biodiesel fuel system. This visible opacity or haze in biodiesel has been found partly to consist of steryl glycosides. They are thought to complex together and in combination with monoglycerides and/or diglycerides in the fuel to produce aggregates that precipitate out of solution and settle in fuel tanks and clog fuel filters.

Lipases are attractive catalysts for the production of biodiesel. However, biodiesel is traditionally made by alkaline catalyzed transesterification of the feedstock with an alcohol. In FAME this alcohol is methanol. Any free fatty acids in the feedstock are typically converted to biodiesel by acidic catalysis. During the alkaline transesterification process to produce biodiesel, acylated steryl glycosides are, at least to some degree, converted to steryl glycosides. Hence, feedstocks with a high content of acylated steryl glycosides can be expected to yield biodiesel with a high content of steryl glycosides.

The amount of steryl glycoside and acylated steryl glycoside is enriched in gums produced by degumming of oils and is similarly expected to be enriched in soapstock and acid oils, and biodiesel made from these feedstocks may contain relatively high levels of steryl glycosides. The amounts of steryl glycosides and acylated steryl glycosides are present in the mg/kg range and have in crude oil been shown to be dependent on the origin. Analysis of biodiesel precipitates/solids has revealed that steryl glycosides may constitute as high as 68% of the material.

In some embodiments the invention relates to a process, wherein the concentration of steryl glycoside in the composition prior to contacting it with the enzyme is at least 30 ppm; at least 40 ppm; at least 50 ppm; at least 60 ppm; at least 70 ppm; at least 80 ppm; at least 90 ppm; at least 100 ppm; at least 150 ppm; at least 200 ppm; at least 250 ppm; or at least 300 ppm.

24 ppm is the upper limit for the amount of total contamination (insoluble matter) in biodiesel according to the international standard (EN 14214) that describes the minimum requirements for biodiesel.

In some embodiments the invention relates to a process, wherein the concentration of steryl glycoside in the composition after contacting it with the enzyme is below 50 ppm; below 40 ppm; below 30 ppm; below 25 ppm; below 24 ppm; below 23 ppm; below 22 ppm; below 21 ppm; below 20 ppm; below 15 ppm; below 10 ppm; or below 5 ppm.

ppm in the context of the present invention means mg/kg.

In some embodiments the invention relates to a process, wherein the concentration of steryl glycoside in the composition after contacting it with the enzyme is reduced by at least 20%, preferably by at least 30% or at least 50%, more preferably by at least 70%, and even more preferably by at least 80%.

Enzyme being Capable of Acylating Steryl Glycoside

The enzyme to be used in the process of the present invention is an enzyme being capable of acylating steryl glycoside. Preferably, the steryl glycoside is acylated with an acyl group from fatty acid alkyl ester. I.e., preferably, the fatty acid alkyl ester in the composition is the acyl donor. However, as described below, in some embodiments, a further acyl donor may be added to the composition.

The enzyme to be used in the process of the present invention is preferably a lipase. I.e., an enzyme that has lipase activity, generally classified as EC 3.1.1.x. Such enzyme may catalyze reactions such as hydrolysis, interesterification, transesterefication, esterification, alcoholysis, acidolysis and aminolysis. Lipases particularly relevant for the present invention may be those that catalyze the esterification of fatty acids or transesterification of fatty acid esters in the presence of alcohol to yield fatty acid alkyl ester. In a preferred embodiment, the enzyme is an enzyme classified as EC 3.1.1.3. However, many other enzymes classified as EC 3.1.1.x, e.g. cutinases, generally classified as EC 3.1.1.74, will also be relevant.

In the context of the present invention, phospholipases, i.e., enzymes having phospholipase activity, constitute a subgroup of lipases (EC 3.1.1.x). Phospholipases may catalyze reactions that lead to the formation of fatty acid alkyl ester and is for the purpose of the present invention also defined as a lipase.

Acyltransferase as used herein means an enzyme which has acyltransferase activity, generally classified as EC 2.3.1.x, whereby the enzyme is capable of transferring an acyl group from an acyl donor to one or more acyl acceptor substrates selected from: any compound comprising a hydroxyl group (—OH) i.e. alcohols such as sterol, stanol, glycerol etc; carbohydrate; protein; protein subunit. Enzymes classified as acyltransferase will in many cases have other activities as well, such as lipase activity, e.g., phospholipase activity. Lipid acyltransferases catalyze reactions such as transesterification and alcoholysis, and thus said enzyme may catalyze reactions that lead to the formation of fatty acid alkyl ester and are also relevant in the process of the present invention. Reactions may in the presence of water in certain embodiments of the invention be catalyzed by acyltransferase.

In one embodiment of the process of the invention, the enzyme is an acyltransferase. Such enzyme is meant to also include a lipase having acyltransferase activity.

Enzymes suitable for use in a process of the invention, may be obtained from microorganisms, such as filamentous fungi, yeast, or bacteria. In some embodiments the enzyme may be formulated as immobilized products as will be described further below.

For the purpose of the present invention the term "obtained from", as used herein in connection with a specific microbial source, means that the enzyme and consequently the DNA sequence encoding said enzyme is produced by the specific source. The enzyme is then obtained from said specific source by standard known methods enabling the skilled person to obtain a sample comprising the enzyme and capable of being used in a process of the invention. Said standard methods may be direct purification from said specific source or cloning of a DNA sequence encoding the enzyme followed by recombinant expression either in the same source (homologous recombinant expression) or in a different source (heterologous recombinant expression).

Most lipolytic enzymes used as catalysts in organic synthesis are of microbial and fungal origin, and these are readily available by fermentation and basic purification. Lipolytic enzymes extracted from various sources have successfully been used in processes for generating biodiesel. *Candida Antarctica* B lipase immobilized on acrylic resin (Novozym 435) has been the most commonly used enzyme in experiments for the production of biodiesel. However, depending on experimental variables such as substrate, alcohol, water, temperature, pH, re-use etc. different lipolytic enzymes may be utilized.

In certain embodiments the present invention relates to a process, wherein the enzyme is selected from the group containing, preferably from the group consisting of: *Aspergillus* lipase; *Aspergillus niger* lipase; *Thermomyces lanuginosa* lipase; *Candida Antarctica* lipase A; *Candida Antarctica* lipase B; *Candida cylindracae* lipase; *Candida deformans* lipase; *Candida lipolytica* lipase; *Candida parapsilosis* lipase; *Candida rugosa* lipase; *Corynebacterium acnes* lipase; *Cryptococcus* spp. S-2 lipase; *Fusarium culmorum* lipase; *Fusarium heterosporum* lipase; *Fusarium oxysporum* lipase; *Mucor javanicus* lipase; *Rhizomucor miehei* lipase; *Rhizomucor delemar* lipase; *Burkholderia (Pseudomonas) cepacia* lipase; *Pseudomonas camembertii* lipase; *Pseudomonas fluorescens* lipase; *Rhizopus* lipase; *Rhizopus arrhizus* lipase; *Staphylococcus aureus* lipase; *Geotrichium candidum* lipase; *Hyphozyma* sp. lipase; *Klebsiella oxytoca* lipase; and wildtype orthologs and homologs thereof; and variants thereof that have an amino acid sequence that is at least 60%; at least 70%, at least 75%, at least 80%, at least 85%; at least 90%, at least 92%; at least 94%; at least 95%, at least 96%; at least 97%; at least 98% or at least 99% identical to any of those wildtype enzymes.

In certain embodiments the present invention relates to a process, wherein the enzyme is selected from the group deposited in NCBI's Genebank database as accession numbers: YP_890535 (GID: 118468600 as also described in WO05/056782; *M. smegmatis*); NP_436338.1 (GID: 16263545; *Sinorhizobium meliloti*); ZP_01549788.1 (GID: 118592396; *Stappia aggregate*); NP_066659.1 (GID: 10954724; *Agrobacterium rhizogenes*); YP_368715.1 (GID: 78065946; *Burkholderia* sp); YP_674187.1 (GID: 110633979; *Mesorhizobium* sp.); NP_532123.1 (GID: 17935333; *Agrobacterium tumefaciens*); *Agrobacterium rhizogenes* (Q9 KWA6); *A. rhizogenes* (Q9 KWB1); *A. tumefaciens* (Q8UFG4); *A. tumefaciens* (Q8UACO); *A. tumefaciens* (Q9ZI09); *A. tumefaciens* (ACA); *Prosthecobacter dejongeii* (RVM04532); *Rhizobium. loti* (Q98MY5); *R. meliloti* (Q92XZ1); *R. meliloti* (Q9EV56), *R. rhizogenes* (NF006), *R. rhizogenes* (NF00602875), *R. solanacearum* (Q8XQI0); *Sinorhizobium meliloti* (RSM02162); *Sinorhizobium meliloti* (RSM05666); *Mesorhizobium loti* (RMLO00301); *A. rhizogenes* (Q9 KWA6); *A. rhizogenes* (Q9 KWB1); *Agrobacterium tumefaciens* (AAD02335); *Mesorhizobium* loti (Q98MY5); *Mesorhizobium loti* (ZPOO 197751); *Ralstonia solanacearum* (Q8XQI0); *Ralstonia eutropha* (ZPOO 166901); *Moraxella bovis* (AAK53448); *Burkholderia cepacia* (ZP00216984); *Chromobacterium violaceum* (Q7NRP5); *Pirellula* sp. (NP_865746); *Vibrio vulnificus* (AA007232); *Salmonella typhimurium* (AAC38796); *Sinorhizobium meliloti* (SMal993); *Sinorhizobium meliloti* (Q92XZ1); *Sinorhizobium meliloti* (Q9EV56); and wildtype orthologs and homologs thereof; and variants thereof that have an amino acid sequence that is at least 60%; at least 70%, at least 75%, at least 80%, at least 85%; at least 90%, at least 92%; at least 94%; at least 95%, at least 96%; at least 97%; at least 98% or at least 99% identical to any of those wildtype enzymes.

The identity may be calculated based on either amino acid sequences or nucleotide sequences.

The relatedness between two amino acid sequences or between two nucleotide sequences is described by the parameter "identity". For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Immobilized Enzymes

The use of immobilized enzymes in oils and fats processing are experiencing significant growth due to new technology developments that have enabled cost effective methods. A fundamental advantage of immobilized enzymes is that they can be recovered and re-used from a batch process by simple filtration. Further, packing of immobilized enzymes in columns allows for easy implementation of a continuous process. Immobilized enzymes generally also have a positive effect on operational stability of the catalyst (compared to free enzymes), it makes handling easier (compared to free enzyme powder), and it allows operation under low-water conditions (compared to liquid formulated enzymes).

Various ways of immobilizing enzymes, e.g., lipases, are well known in the art. A review of lipase immobilization is found in "*Immobilized lipase reactors for modification of fats and oils—a review*" Malcata, F X., et al. (1990) Journal of American Oil Chemist's Society Vol. 67 p. 890-910, where examples of representative lipase immobilizing carriers are illustrated, including inorganic carriers such as diatomaceous earth, silica, porous glass, etc.; various synthetic resins and synthetic resin ion exchangers; and natural polysaccharide carriers such as cellulose and cross-linked dextrin.

In some embodiments the invention relates to a process for reducing the content of steryl glycoside in a fatty acid alkyl ester composition, wherein the lipase is covalently or non-covalently immobilized on a carrier; or alternatively by entrapment in natural or synthetic matrices, such as sol-gels, alginate, and carrageenan; by cross-linking methods such as in cross-linked enzyme crystals (CLEC) and cross-linked enzyme aggregates (CLEA); or by precipitation on salt crystals such as protein-coated micro-crystals (PCMC).

In some embodiments the invention relates to a process for reducing the content of steryl glycoside in a fatty acid alkyl ester composition, wherein the carrier is a hydrophilic carrier selected from the group containing, preferably from the group consisting of: porous in-organic particles composed of alumina, silica and silicates such as porous glass, zeolites, diatomaceous earth, bentonite, vermiculite, hydrotalcite; and porous organic particles composed of carbohydrate polymers such as agarose or cellulose.

In some embodiments the invention relates to a process for reducing the content of steryl glycoside in a fatty acid alkyl ester composition, wherein the carrier is a hydrophobic carrier. Such hydrophobic carrier preferably contains at least one material selected from the group containing, preferably from the group consisting of: synthetic polymers such as polyacrylates, polymethacrylates, nylon, polyethylene, polypropylene or polystyrenes (such as crosslinked polystyrenes); hydrophobic silica; and activated carbon. Many synthetic hydrophobic polymer carriers are copolymers containing several different monomer components.

Alternatively, enzymes expressed intra or extra-cellularly by the microbe are used after immobilization of the nonviable cells and used as an enzyme source. This way the cells are used as the carrier material for the enzyme.

Enzymes in solid form, such as immobilized lipases, may be used in some embodiments of the invention and examples of commercially available immobilized lipases include the ones sold under the trade names LIPOZYME TL IM™, LIPOZYME RM IM™, and Novozym 435 (Novozymes A/S).

In case the reaction is carried out with liquid formulations of an enzyme (in contrast to an immobilized enzyme) the enzyme can be recovered for multiple uses by either separation of the aqueous phase containing the enzyme or by using a membrane reactor. In a membrane reactor the end-product is separated from the enzyme by using a membrane filtration system.

Feedstocks

Any oils and fats of vegetable or animal origin comprising fatty acids may be used as basis for generating the fatty acid alkyl ester composition to be used in the process of the invention. Fatty acids (FA) are in the context of the invention defined as free fatty acids (FFA) and/or fatty acid residues. Fatty acid residues may be derived from polar lipids such as phospholipids; from non-polar lipids such as triglycerides, diglycerides, and monoglycerides; and esters comprising fatty acids such as sterol ester or acylated steryl glycosides; or any combination thereof.

The fatty acids may be free fatty acids and/or fatty acid residues. The fatty acid residues may be derived from triglycerides, diglycerides, monoglycerides, or any combination thereof. The fatty acid residues may be derived from esters comprising fatty acids such as sterol ester, stanol ester, or any combination thereof.

The feedstock may be oil selected from the group consisting of: Algae oil, grape seed oil, jatropha oil, jojoba oil, castor oil, coconut oil (copra oil), corn oil, cottonseed oil, flax oil, fish oil, hemp oil, mustard oil, canola oil, palm oil, palm stearin, palm olein, palm kernel oil, peanut oil, rapeseed oil, rice bran oil, safflower oil, soybean oil, sunflower oil and oil from halophytes, or any combination thereof.

The feedstock may be fat selected from the group consisting of: Animal fat, including tallow from pigs, beef and sheep, lard, yellow grease, chicken fat, or any combination thereof.

The feedstock may be crude, refined, bleached, deodorized, degummed, or any combination thereof.

Food quality oils and fats are expensive which leads to a reduced viability for their use in the production of biodiesel, and therefore, waste and by-products from their processing as well as non-food grade oils and fats, have become increasingly attractive feedstock for fatty acid alkyl ester. Soap stock is the fraction of oil obtained in an oil refinery by treating the oil with a base to convert free fatty acids to soaps (e.g. sodium soaps). The soap stock usually contains a fraction of glycerides beside the soaps. Acid oil is the by-product from the oil refinery produced by acidification of soap stock to solubilize the soaps. It mainly contains free fatty acids (FFA) and acylglycerols. Distillates like Palm Fatty Acid Distillate is the by-product from oil refining coming from a distillation process used to eliminate free fatty acid from the oil.

The feedstock may be an intermediate product, a waste product or a by-product of oil or fat refining selected from the group consisting of: soap stock; acid oil; fatty acid distillates such as palm fatty acid distillate (PFAD), soy fatty acid distillate, rapeseed fatty acid distillate, rice bran fatty acid distillate, poultry fat fatty acid distillate, beef tallow fatty acid distillate, etc.; gums from degumming; by-products from the production of Omega-3 fatty acids derivates from fish oil; fat trap grease; free fatty acids like oleic acid; or fractions of oil obtained by physical separations; or any combinations thereof.

Short-Chain Alcohols

A short-chain alcohol is an alcohol having 1 to 5 carbon atoms ($C_1$-$C_5$) like e.g. short-chain primary alcohols such as methanol (MeOH), ethanol (EtOH), 1-propanol (PrOH), 1-butanol (n-BuOH), and 1-pentanol; and short-chain secondary alcohols such as 2-propanol (iPrOH).

A short-chain alcohol used for the production of biodiesel to be used in the process of the invention may be selected from the group consisting of: short-chain primary alcohols such as methanol (MeOH), ethanol (EtOH), 1-propanol (PrOH), 1-butanol (n-BuOH), and 1-pentanol; short-chain secondary alcohols such as 2-propanol (iPrOH); or any combination thereof.

Fatty Acid Alkyl Ester Compositions

Any oils and fats of vegetable or animal origin comprising fatty acids as described in the section "Feedstocks" supra may be used as basis for generating the fatty acid alkyl ester composition. Fatty acid alkyl ester compositions having reduced amounts of steryl glycosides may be obtained by subjecting an already made fatty acid alkyl ester composition or biodiesel to the process according to the invention.

In some embodiments the invention relates to a process, wherein the fatty acid alkyl ester composition is selected from a group consisting of: fatty acid methyl ester; fatty acid ethyl ester; fatty acid propyl ester; fatty acid butyl ester; fatty acid pentyl ester; or any combinations thereof. All isomers of these are meant to be included. E.g., fatty acid propyl ester can be an ester of the primary alcohol, i.e. fatty acid 1-propyl ester, or an ester of the secondary alcohol, i.e. fatty acid isopropyl ester.

In some embodiments the invention relates to a process, where at least 80 wt. % of fatty acids in the composition are in the form of fatty acid alkyl ester selected from a group consisting of: fatty acid methyl ester; fatty acid ethyl ester; fatty acid propyl ester; fatty acid butyl ester and fatty acid pentyl ester; or any combination thereof.

In some embodiments the invention relates to a process, where the composition comprises at least 80 wt. % fatty acid alkyl ester selected from a group consisting of: fatty acid methyl ester; fatty acid ethyl ester; fatty acid propyl ester; fatty acid butyl ester and fatty acid pentyl ester; or any combination thereof.

In some embodiments the invention relates to a process, where at least one further acyl donor is present.

It is apparent that the fatty acid alkyl ester composition of the invention may be used in its own capacity. However, it may also be used in blends together with other fuels, both that of other fatty acid alkyl ester compositions and/or petroleum-based diesel fuel. The blending may be performed before, during or after the enzymatic process of the invention.

In one embodiment, the invention relates to a process of reducing the content of steryl glycoside in a composition comprising fatty acid alkyl ester, wherein at least 80 wt. % of fatty acids in the composition are in the form of fatty acid alkyl ester, which comprises a step of contacting the composition with an enzyme being capable of acylating the steryl glycoside, or to any embodiment of such process described above, which further comprises a step of using the enzyme treated fatty acid alkyl ester composition in a fuel composition. Such fuel composition may further comprise petroleum-based diesel fuel.

In one embodiment, the invention relates to a process, wherein the composition to be contacted with the enzyme further comprises petroleum-based diesel fuel.

In one embodiment, the invention relates to a process, which further comprises a step of mixing the enzyme treated composition with petroleum-based diesel fuel.

In one embodiment, the invention relates to a process, which further comprises a step of using the enzyme treated composition in a fuel composition.

In some embodiments the invention relates to a fatty acid alkyl ester composition with a reduced amount of steryl glycosides.

In some embodiments the invention relates to a fatty acid alkyl ester composition with a reduced amount of steryl glycosides wherein the concentration of steryl glycoside is below 50 ppm; below 40 ppm; below 30 ppm; below 25 ppm; below 24 ppm; below 23 ppm; below 22 ppm; below 21 ppm; below 20 ppm; below 15 ppm; below 10 ppm; or below 5 ppm.

In some embodiments the invention relates to a fuel comprising the fatty acid alkyl ester composition.

In some embodiments the invention relates to a fuel further comprising petroleum-based diesel fuel.

The content of water must according to EN 14214 be below 500 ppm. In some embodiments the invention relates to a fatty acid alkyl ester composition wherein the content of water is below 500 ppm.

The reduced amount of steryl glycosides in the fatty acid alkyl ester composition of the invention may furthermore contribute to an overall reduction of the filter blocking tendency of fuel or fuel blends based wholly or partly on the fatty acid alkyl ester composition of the invention, respectively.

In some embodiments the invention relates to use of the process for reducing the filter blocking tendency of fuel and/or fuel blends.

In some embodiments the invention relates to use of the fatty acid alkyl ester composition for reducing the filter blocking tendency of fuel and/or fuel blends.

The process of reducing the content of steryl glycosides may be part of the process of producing biodiesel where it may be included as one of the last steps. Formation and amount of steryl glycoside precipitates are dependant on various factors e.g. selection of feedstock. It may also not be visible immediately after biodiesel synthesis why it would be desirable to postpone removal of steryl glycosides until later if required at all. It is thus contemplated that removal of steryl glycosides may take place at biodiesel production plants, in storage containers, in transportation containers, in gas/petrol station containers, in fuel tanks of vehicles/planes/trains etc. The enzyme may be added as an additive in the form of a liquid or in an immobilized form directly to the biodiesel. It may also be incorporated into a filter or a column used at any of the places to pour or drain biodiesel into or from a container.

The present invention is further described by the following examples that should not be construed as limiting the scope of the invention.

Materials and Methods

Chemicals used as buffers and substrates were commercial products of at least reagent grade. All chemicals, unless otherwise indicated, were obtained from Sigma-Aldrich or a similar commercial source and used without further purification.

EXAMPLES

Example 1

A Change in the Amount of Steryl Glycoside (SG) was Observed in Biodiesel Incubated with Immobilized Lipase Two different samples of palm biodiesel obtained from Desmet Ballestra (Belgium) were used: a "Clear" with a low SG-content and a "Hazy" with a high SG-content. We studied the effect of using two different immobilized lipases from Novozymes: Novozym 435, which is *Candida antarctica* lipase B (CALB) immobilized on a hydrophobic polymer; and NS40042, which is CALB on a silica carrier.

Reactions were carried out in 100 mL closed crew-cap conical flasks placed for 22 hours in a water bath at 50° C. with 200 rpm shaking. 20 mL biodiesel was incubate with immobilized 1 g enzyme; 1 g carrier without enzyme; or nothing (i.e. blank, only biodiesel incubating for 22 h). After incubation, biodiesel was removed from the immobilized enzyme by decantation.

For SG-analysis, the biodiesel sample (2 g) was applied on a solid-phase extraction (SPE) column (1000 mg, 6 mL, silica cartridge from GracePure). After eluting biodiesel with heptane, SG could be eluted with heptane/EtOAc/iPrOH (70:25:5, v/v/v), followed by THF/EtOH (50:50, v/v). The eluants were evaporated to dryness, followed by derivatization with BSTFA, 1% TMS for 30 minutes at 80° C. Gas chromatographic (GC) analysis on a DB-5HT column (15 meter, 0.32 millimeter, 0.1 micrometer) then allowed quantification of free steryl glycosides (FSG) against an internal standard, betulinol.

TABLE 1

Steryl glycoside (SG) content in ppm.

|  | Clear biodiesel | Hazy biodiesel |
| --- | --- | --- |
| Blank (control) | 17 | 117 |
| Novozym 435 carrier (control) | 26 | 104 |
| Novozym 435 | 19 | 17 |
| NS40042 carrier (control) | 2 | 8 |
| NS40042 | 2 | 7 |

These results show that enzymatic treatment of biodiesel significantly reduced the content of steryl glucoside. For "Clear" biodiesel, only NS40042 seems to work. However, the control experiment with NS40042 carrier shows that SG adsorbs to silica. Therefore, it is uncertain if the observed effect in samples incubated with NS40042 is due to the enzyme or the carrier. On the other hand, for Novozym 435 on "Hazy" biodiesel, there is an effect of the immobilized enzyme and no effect of the carrier itself.

Example 2

A Change in the Amounts of Steryl Glycoside (SG) and Acylated Steryl Glycoside (ASG) was Observed in Biodiesel Incubated with Immobilized Lipase To get the full picture of what is happening, we also looked for ASG-content in the enzyme treated samples. If the enzyme is removing SG by converting it to ASG, we should be able to see an increase in ASG-level.

Biodiesel was treated with immobilized enzyme in batch experiments as described in Example 1 with the following exceptions:
1) Only samples of "Hazy" biodiesel were treated with the enzyme Novozym 435.
2) Incubation conditions were shaking at 150 rpm for 43 hours.
3) SG and ASG analysis of the samples were carried out by "ASG Analytical Service Ge-sellschaft mbH, Trentiner Ring 30, D-86356 Neusaess, Germany".

TABLE 2

Acylated steryl glycoside (ASG) and steryl glycoside (SG) content in ppm.

|  | Physical appearance | ASG | SG |
| --- | --- | --- | --- |
| Novozym 435 carrier (control) | Very hazy | 71 | 147 |
| Novozym 435 | Clear | 147 | 21 |

The result shows that the SG level is reduced significantly in the biodiesel sample treated with the enzyme Novozym 435 in comparison with the sample treated with the inert Novozym 435 carrier. It is furthermore demonstrated that the amount of ASG simultaneously is increased in the biodiesel sample treated with the enzyme compared to the sample treated with an inert carrier.

The invention claimed is:
1. A process of reducing the content of steryl glycosides in a biodiesel composition comprising
providing a biodiesel composition comprising steryl glycoside and fatty acid alkyl ester, wherein at least 80 weight % of fatty acids in the composition are in the form of fatty acid alkyl ester, and
contacting the biodiesel composition with an enzyme capable of acylating the steryl glycoside to provide an enzyme treated composition having a reduced content of steryl glycoside, wherein the fatty acid alkyl ester is acyl donor to acylate steryl glycoside to soluble acylated steryl glycoside,
wherein the concentration of steryl glycoside in the composition prior to contacting it with the enzyme is at least 30 ppm.
2. The process of claim 1, wherein the steryl glycoside is derived from a sterol selected from a group consisting of: a phytosterol, a zoosterol, the corresponding saturated forms of said sterol (stanol); and any combinations thereof.
3. The process of claim 1, wherein the sterol is campesterol, sitosterol, stigmasterol, avenasterol, brassicasterol, desmosterol, fucosterol, sargasterol, or cholesterol.
4. The process of claim 1, wherein the concentration of steryl glycoside in the enzyme treated composition is below 24 ppm.
5. The process of claim 1, wherein at least 80 weight % of fatty acids in the composition are in the form of fatty acid alkyl ester selected from a group consisting of: fatty acid methyl ester; fatty acid ethyl ester; fatty acid propyl ester; fatty acid butyl ester and fatty acid pentyl ester; or any combination thereof.
6. The process of claim 1, wherein the enzyme is a lipase classified as EC 3.1.1.
7. The process of claim 1, wherein the enzyme is a lipase classified as EC 3.1.1.3.
8. The process of claim 1, wherein the enzyme is selected from the group consisting of: *Aspergillus* lipase; *Aspergillus niger* lipase; *Thermomyces lanuginosa* lipase; *Candida antarctica* lipase A; *Candida antarctica* lipase B; *Candida* cylindracae lipase; *Candida deformans* lipase; *Candida lipolytica* lipase; *Candida parapsilosis* lipase; *Candida rugosa* lipase; *Corynebacterium acnes* lipase; *Cryptococcus* spp. S-2 lipase; *Fusarium culmorum* lipase; *Fusarium heterosporum* lipase; *Fusarium oxysporum* lipase; *Mucor javanicus* lipase; *Rhizomucor miehei* lipase; *Rhizomucor delemar* lipase; *Burkholderia* (*Pseudomonas*) *cepacia* lipase; *Pseudomonas camembertii* lipase; *Pseudomonas fluorescens* lipase; *Rhizopus* lipase; *Rhizopus arrhizus* lipase; *Staphylococcus aureus* lipase; *Geotrichium candidum* lipase; *Hyphozyma* sp. lipase; *Klebsiella oxytoca* lipase; and variants thereof.

9. The process of claim 1, wherein the enzyme is a *Candida antarctica* lipase B or a variant thereof.

10. The process of claim 1, wherein the enzyme is immobilized covalently or non-covalently immobilized on a carrier or by entrapment in a natural or synthetic matrix.

11. The process of claim 10, wherein the enzyme is immobilized on a hydrophilic carrier selected from the group consisting of: porous in-organic particles composed of alumina, silica, silicates, zeolites, diatomaceous earth, bentonite, vermiculite, hydrotalcite; and porous organic particles composed of carbohydrate polymers.

12. The process of claim 10, wherein the enzyme is immobilized on a hydrophobic carrier containing at least one material selected from the group consisting of: synthetic polymers; hydrophobic silica; and activated carbon.

13. The process of claim 1, wherein the composition further comprises petroleum-based diesel fuel.

14. The process of claim 1, further comprising mixing the enzyme treated composition with petroleum-based diesel fuel.

15. The process of claim 1, wherein the concentration of steryl glycoside in the composition prior to contacting it with the enzyme is at least 50 ppm.

16. The process of claim 1, wherein the concentration of steryl glycoside in the composition prior to contacting it with the enzyme is at least 80 ppm.

17. The process of claim 1, wherein the concentration of steryl glycoside in the composition prior to contacting it with the enzyme is at least 100 ppm.

18. The process of claim 1, wherein the concentration of steryl glycoside in the composition prior to contacting it with the enzyme is at least 150 ppm.

19. The process of claim 1, wherein the concentration of steryl glycoside in the enzyme treated composition is below 20 ppm.

20. The process of claim 1, wherein the concentration of steryl glycoside in the enzyme treated composition is below 15 ppm.

* * * * *